US010206713B2

(12) United States Patent
Olsen et al.

(10) Patent No.: US 10,206,713 B2
(45) Date of Patent: Feb. 19, 2019

(54) BONE FIXATION DEVICE

(71) Applicant: ApMed LLC, Osage Beach, MO (US)

(72) Inventors: Ron A. Olsen, Queen Creek, AZ (US);
Robert Horneff, Vancouver, WA (US);
Carey Bryant, Hernando, MS (US)

(73) Assignee: APMED LLC, Osage Beach, MO (US)

( * ) Notice: Subject to any disclaimer, the term of this patent is extended or adjusted under 35 U.S.C. 154(b) by 975 days.

(21) Appl. No.: 14/558,290

(22) Filed: Dec. 2, 2014

(65) Prior Publication Data

US 2016/0151099 A1   Jun. 2, 2016

(51) Int. Cl.
*A61B 17/60* (2006.01)

(52) U.S. Cl.
CPC .................... *A61B 17/60* (2013.01)

(58) Field of Classification Search
CPC ............................ A61B 17/60; A61B 17/8047
See application file for complete search history.

(56) References Cited

U.S. PATENT DOCUMENTS

| 7,507,240 | B2 | 3/2009 | Olsen |
| 7,507,250 | B2 | 3/2009 | Lennox |
| 7,575,575 | B2 | 8/2009 | Olsen |
| 7,588,571 | B2 | 9/2009 | Olsen |
| 2008/0147124 | A1* | 6/2008 | Haidukewych .... A61B 17/8004 606/280 |
| 2014/0276815 | A1* | 9/2014 | Riccione ............ A61B 17/6416 606/54 |

OTHER PUBLICATIONS webpage, http://www.wmt.com/footandankle/FA450-1207.asp, printed Mar. 6, 2015.

* cited by examiner

*Primary Examiner* — David Bates
(74) *Attorney, Agent, or Firm* — Kunzler, PC

(57) ABSTRACT

A bone fixation device that includes a rail body housing that has a top portion, a bottom portion, a first end portion, a second end portion, and a rail channel extending along a longitudinal axis of the rail body housing. The rail channel is defined between the top portion, the bottom portion, the first end portion, and the second end portion. The movable clamp assembly is movably coupled to the rail body housing within the rail channel and the position of the movable clamp assembly within the rail channel is adjustable. The movable clamp assembly also includes at least one semi-spherical collet defining a central channel configured to receive a bone fastener and orient the bone fastener in any of a plurality of orientations with respect to the rail body housing.

21 Claims, 10 Drawing Sheets

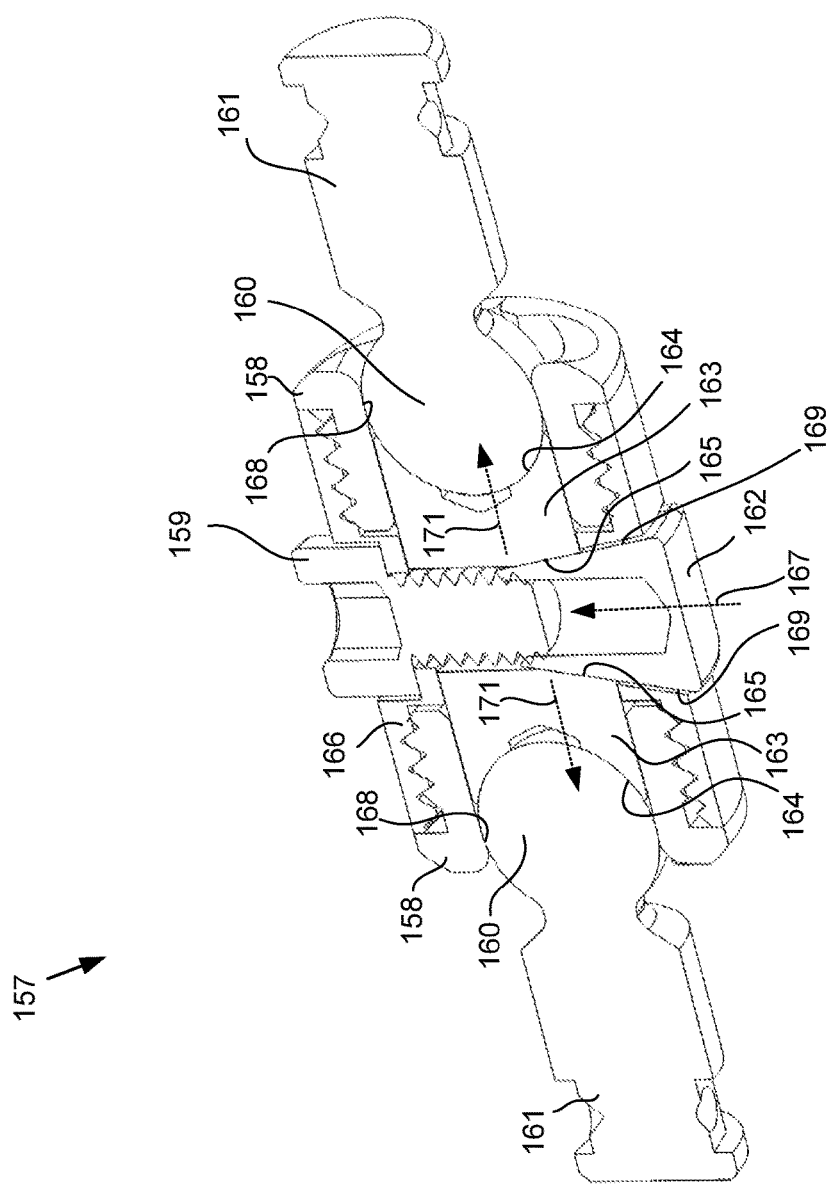

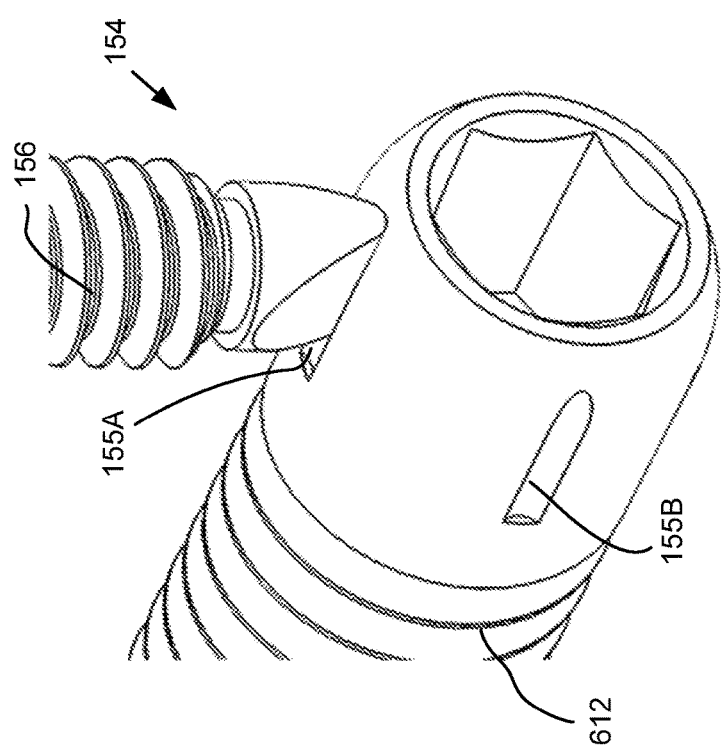

BONE FIXATION DEVICE

FIELD

This disclosure relates generally to bone fixation devices, and more particularly to adjustable bone splint devices.

BACKGROUND

When fractured bones are properly splinted, they often are able to heal in an appropriate manner, thereby simulating the shape and function of the previously uninjured, natural bone. Bone fixation devices are often employed in the treatment of fractures of bones such as bones in the foot, hand, maxiofacial regions, or other extremities, but also with a variety of different bone types. Such fixation devices are often known as splint devices.

Typical splint devices feature a longitudinal support body and a pair of clamps mounted on the longitudinal support body. A clamp can be moved along the body through the use of an adjustable lead screw extending through the support body. Bone screws that are transverse to the longitudinal body connect to the clamps and secure the splint to the bone. By adjusting the lead screw, the position of the clamps can be moved with respect to the longitudinal support, thereby adjusting the size and configuration of the splint and the location of the transverse bone screws.

One limitation to typical bone fixation devices, such as adjustable splints, is that the clamp connected to the longitudinal support is only movable in an axial, linear direction with respect to the longitudinal support. The bone screws are also limited in their orientation. This dynamic limits the practitioner's options when attempting to set one or more bones using such splint devices.

Another limitation with typical splint devices relates to the positioning of one longitudinal support with respect to another longitudinal support. Such positioning typically results in limited movement, again reducing treatment options.

Yet another limitation associated with previous splint devices is that the lead screw used to provide adjustment of the bone clamps is retained in the longitudinal support body through the use of complicated multi-part systems that require a number of different parts to be added to the device assembly.

Another disadvantage of typical devices is that the lead screw of the devices projects outwardly from the elongated body, thereby exposing the lead screw to being inadvertently turned. Further, conventional splint devices generally require multiple different tools to assemble, actuate, and/or otherwise use the splint devices, thereby increasing the complexity and implementation of conventional splint devices.

SUMMARY

From the foregoing discussion, it should be apparent that a need exists for a bone fixation apparatus and system that overcome the limitations of conventional splint assemblies. Beneficially, such an apparatus and system would provide a flexible and convenient manner to treat the fracture and/or deformation of bones.

The subject matter of the present application has been developed in response to the present state of the art, and in particular, in response to the problems and needs in the art that have not yet been fully solved by currently available splint assemblies. Accordingly, the present disclosure has been developed to provide a bone fixation device that overcomes many or all of the above-discussed shortcomings in the art.

Disclosed herein is one embodiment of a bone fixation device. The bone fixation device includes a rail body housing that has a top portion, a bottom portion, a first end portion, a second end portion, and a rail channel extending along a longitudinal axis of the rail body housing. The rail channel is defined between the top portion, the bottom portion, the first end portion, and the second end portion. The movable clamp assembly is movably coupled to the rail body housing within the rail channel and the position of the movable clamp assembly within the rail channel is adjustable. The movable clamp assembly also includes at least one semi-spherical collet defining a central channel configured to receive a bone fastener and orient the bone fastener in any of a plurality of orientations with respect to the rail body housing.

According to one implementation, the size of the central channel of the at least one semi-spherical collet is adjustable to retain a bone fastener therein and a central axis of the central channel intersects the longitudinal axis of the rail body housing. In one implementation, the longitudinal axis passes through a center-of-gravity of the rail body housing. Further, the at least one semi-spherical collet may include two semi-spherical collets and the movable clamp assembly may further include means for coupling the two semi-spherical collets together such that rotation about the central channel of the semi-spherical collets is prevented.

In one implementation, the bone fixation device further includes a fixed clamp assembly that is longitudinally fixed relative to the rail body. The fixed clamp assembly may have at least one semi-spherical collet defining a central channel that is configured to receive a bone fastener, with the size of the central channel being adjustable to retain a bone fastener therein. A portion of the rail body housing may be flexible to clamp down and around on the semi-spherical collet, thus adjusting the size of the central channel. In another implementation, a central axis of the central channel of the at least one semi-spherical collet of the fixed clamp assembly intersects the longitudinal axis of the rail body housing.

Also disclosed herein is another embodiment of a bone fixation device. The bone fixation device includes a rail body housing that has a first end portion, a second end portion, and a rail channel extending along a longitudinal axis of the rail body housing. The rail channel is defined between the first end portion and the second end portion. The bone fixation device further includes a movable clamp assembly that is movably coupled to the rail body housing within the rail channel, thereby allowing the position of the movable clamp assembly within the rail channel to be adjusted. Still further, the bone fixation device includes a lead bolt and a rotational index indicator. The lead bolt extends parallel to the longitudinal axis within the rail body housing and is threadably engaged with the movable clamp assembly. Accordingly, rotation of the lead bolt causes the movable clamp assembly to move along the longitudinal axis within the rail body housing. The rotational index indicator is coupled to the lead bolt and audibly and/or palpably indicates rotation of the lead bolt.

According to one implementation, the rail body housing includes a top portion and a bottom portion that are detachably coupled together, with the bottom portion having the lead bolt and the top portion having a groove. The bottom carriage portion of the movable clamp assembly may be threadably engaged and may rest on the lead bolt while a top sliding portion that is slidably engaged in the groove. The longitudinal axis may extend between the top portion and the bottom portion of the rail body housing. In one implementation, the movable clamp assembly includes at least one semi-spherical collet defining a central channel that is configured to receive a bone fastener. The size of the central channel is adjustable to retain a bone fastener therein and a central axis of the central channel may intersect the longitudinal axis of the rail body housing.

In one implementation the lead bolt includes an actuator screw cap that rotatably locks the position of the lead bolt in order to secure the translational position of the movable clamp assembly. In yet another implementation, the rail body housing is a first rail body housing and the bone fixation device further comprises a second rail body housing coupled to the first rail body housing, with at least one of a second fixed clamp assembly and a second movable clamp assembly that is coupled within the second rail body housing. The first rail body housing and the second rail body housing may be adaptable to extend in non-parallel directions. In another implementation, the first rail body housing and the second rail body housing are coupled together via a double ball joint and the first rail body housing and the second rail body housing are adaptable to extend in parallel yet offset directions.

In one implementation, the rotational index indicator includes a pin and a biasing element coupled to the pin. The biasing element biases the pin into engagement with one or more grooves circumferentially spaced around an exterior surface of the lead bolt. Rotation of the lead bolt causes audible and/or palpable indications that correspond with predetermined movement of the movable clamp assembly along the longitudinal axis of the bone fixation device. In one implementation, when the pin is biased into bias engagement with a first groove of the exterior surface of the lead bolt, rotation of the lead bolt overcomes the bias engagement and the pin subsequently engages a second groove that is circumferentially adjacent the first groove. The lead bolt may include four equally and circumferentially spaced apart grooves so that quarter turns of the lead bolt correspond with audible and/or palpable indications caused by biased engagement/actuation of the pin with the grooves, wherein each quarter turn corresponds to a predetermined longitudinal position adjustment of the movable clamp assembly.

Further disclosed herein is yet another embodiment of a bone fixation device for treating the deformation of bones. The bone fixation device includes a rail body housing, a movable clamp assembly, a fixed clamp assembly, and a rotational index indicator that is coupled to the rail body housing. The rail body housing includes a top portion, a bottom portion, a first end portion, a second end portion, and a rail channel extending along a longitudinal axis of the rail body housing. The rail channel may be defined between the top portion, the bottom portion, the first end portion, and the second end portion, with the bottom portion of the rail body housing having a lead bolt.

The movable clamp assembly is movably coupled within the rail body housing for securing two first bone fasteners in a first desired orientation. In other words, the movable clamp assembly is translatable along the lead bolt within the rail body housing. The movable clamp assembly may also have a carriage portion that is threadably engaged on the lead bolt and a clamping mechanism that is adapted to secure the first bone fasteners, wherein the clamping mechanism has two semi-spherical collets supported within two sockets. The semi-spherical collets may be independently adjustable relative to each other and the first bone fasteners may extend through a central channel in each of the semi-spherical collets. A central axis of the central channel may intersect the longitudinal axis of the rail body housing.

The fixed clamp assembly is coupled within the rail body housing for securing two second bone fasteners in a second desired orientation. The fixed clamp assembly is translationally fixed within the rail body housing and the fixed clamp assembly has a clamping mechanism that is adapted to secure the second bone fasteners. The clamping mechanism includes two semi-spherical collets supported within two sockets and the semi-spherical collets may be independently adjustable relative to each other. The rotational index indicator audibly and/or palpably indicates rotation of the lead bolt.

According to one implementation, the rail body housing is a first rail body housing and the bone fixation device further includes a second rail body housing that is coupled to the first rail body housing. At least one of a second fixed clamp assembly and a second movable clamp assembly is coupled within the second rail body housing. In yet another implementation, the first rail body housing and the second rail body housing are coupled together via a double ball joint so that first rail body housing and the second rail body housing are adaptable to extend in non-parallel directions. In another implementation, the first rail body housing and the second rail body housing are coupled together via a double ball joint so that the first rail body housing and the second rail body housing are adaptable to extend in parallel yet offset directions.

Also disclosed herein is one embodiment of a collet assembly for a bone fixation device. The collet assembly includes a semi-spherical socket and a semi-spherical collet retained by the socket. The semi-spherical collet includes a central channel that is configured to receive a bone fastener and the size of the central channel is adjustable to retain a bone fastener. The semi-spherical collet has at least one groove. The collet assembly further includes a ring fixed relative to the semi-spherical socket, with the ring being configured to engaged the at least one groove of the semi-spherical collet to restrict rotation of the semi-spherical collet about the central channel of the semi-spherical collet.

In one implementation, the central channel extends through a diameter of the semi-spherical collet and the central channel has a first opening and a second opening. The at least one groove of the semi-spherical collet may be a plurality of apertures that extend from the first and second openings in an alternating fashion, with each of the apertures extending in a radial direction from an exterior surface to the central channel and in a circumferential direction from one of the first opening and the second opening to a region circumferentially adjacent the other of the first opening and the second opening. Such a configuration promotes the application of a substantially uniform clamping pressure around an exterior surface portion of the bone fastener.

Further disclosed herein is one embodiment of a coupler for coupling two bone fixation devices together. The coupler includes a housing, a first end cap coupled to one end of the housing and having an internal surface and an external surface, a set screw that at least partially extends through the housing, and a wedge component that is threadably coupled to the wedge component. As the set screw is tightened, the wedge component is drawn further into the housing. The coupler further includes a ball engagement element that has a first surface and a second surface. The ball engagement element is disposed within the housing so that the first surface is adjacent the wedge component. As the wedge component is drawn further into the housing a side of the wedge component abuts and engages the first surface of the ball engagement element. The coupler still further includes a ball joint that has a ball portion and a shaft portion. The ball portion is at least partially disposed within the housing adjacent the second surface of the ball engagement element and the shaft portion extends through the first end cap and is configured to connect to a bone fixation device. As the wedge component abuts and engages the first surface of the ball engagement feature, the second surface of the ball engagement feature abuts and engages the ball portion of the ball joint, thereby securing the ball portion of the ball joint between the second surface of the ball engagement feature and the internal surface of the first end cap.

In one implementation, the external surface of the first end cap has a plurality of lobes that are circumferentially spaced apart. The shaft portion of the ball joint is receivable within the lobes to allow the shaft portion of the ball joint to extend from the first end cap in predetermined extension directions. In one implementation, the housing of the first end cap includes a longitudinal axis and the plurality of lobes are configured to provide a 45 degree angle between the longitudinal axis of the housing and the extension direction of the shaft portion of the ball joint. In yet another implementation, the first end cap is a first end cap and the one end of the housing to which the first end cap is coupled is a first end of the housing. Also, the ball engagement element is a first ball engagement element and the ball joint is a first ball joint, with the side of the wedge component being a first side. In such an implementation, the coupler may further include a second end cap, a second ball engagement element, and a second ball joint disposed on a second side of the wedge component for connecting a second bone fixation device to the second end of the coupler. In another implementation, a first rail body housing and a second rail body housing may be coupled together via the coupler with the double ball joint so that the first rail body housing and the second rail body housing are adaptable to extend in parallel yet offset directions.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which:

FIG. 4E is a perspective cross-sectional view of the double ball joint depicted in FIG. 4D;

FIG. 6 is a perspective view of one embodiment of a rotational index indicator;

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

Illustrated in FIGS. 1-8 are several representative embodiments of a bone fixation device for treating the fracture/deformation of bones, which embodiments also include one or more methods of treating the fracture of bones. As described herein, the bone fixation device provides several significant advantages and benefits over other splints and methods for treating the fracture/deformation of bones. However, the recited advantages are not meant to be limiting in any way, as one skilled in the art will appreciate that other advantages may also be realized upon practicing the present disclosure.

Figure 1:
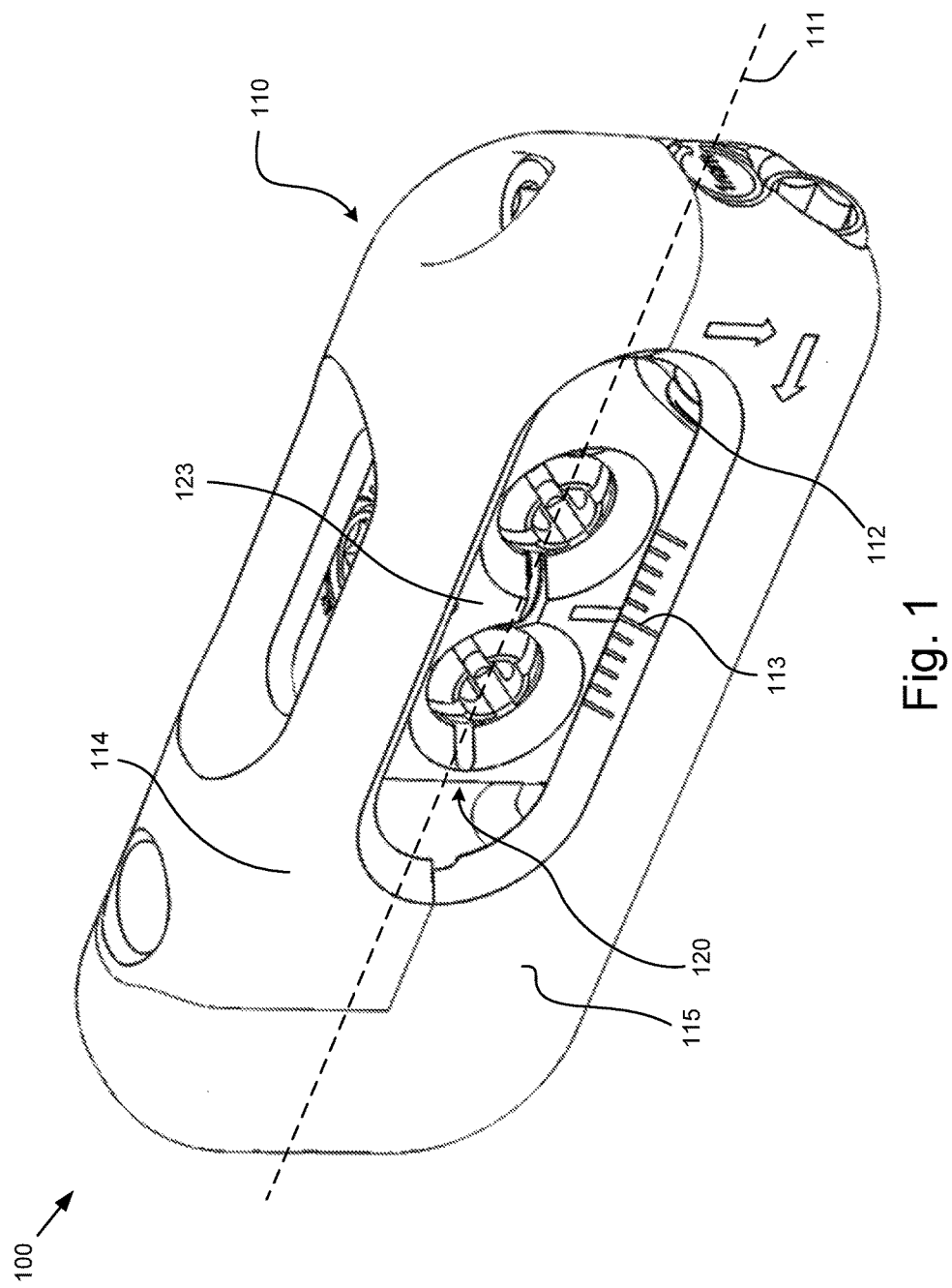
FIG. 1 is a perspective view of one embodiment of a bone fixation device that includes a movable clamp assembly.

FIG. 1 is a perspective view of one embodiment of a bone fixation device 100, which can be a rail body, that includes a movable clamp assembly 120 and a rail body housing 110. The movable clamp assembly 120 is coupled within the rail body housing 110 and is controllably movable along a longitudinal axis 111 of the rail body housing 110. The movable clamp assembly 120 includes a clamping mechanism 123 that secures at least one first bone fastener (not depicted) in a first desired orientation. Additional details regarding the clamping mechanism 123 and the bone fasteners are included below with reference to the remaining figures.

The rail body housing 110 may be assembled or manufactured from two portions 114, 115. In one embodiment, the rail body housing 110 includes a top portion 114 and a bottom portion 115 that are coupled together via a fastener or other coupling mechanism. For example, upon assembly of the bone fixation device 100 the movable clamp assembly 120 may be placed on the bottom portion 115 (e.g., engaged with the lead bolt 112) and the top portion 114 may be subsequently placed over and partially around the movable clamp assembly 120 to partially enclose movable clamp assembly 120. In one embodiment the two portions 114, 115 may be substantially permanently coupled together and in another embodiment the two portions 114, 115 may be detachably coupled to allow a user to repair, clean, or replace the movable clamp assembly 120.

In one embodiment, the movable clamp assembly includes carriage portion 321, 322 (see FIG. 3) and a clamping mechanism portion 123. Additional details regarding the carriage portions 321, 322 and the clamping mechanism are included below with reference to the remaining figures. In one embodiment, the rail body housing also 110 includes a lead bolt 112 (only partially visible in FIG. 1, see FIGS. 2 and 3) which is threadably engaged with the carriage portion of the movable clamp assembly 120. By rotating the lead bolt 112, the movable clamp assembly 120 translates along the longitudinal axis 111 within the rail body housing 110 to a desired position. In one embodiment, the rail body housing 110 may also have visual position indicators 113 that allow a user to accurately position the movable clamp assembly 120 with respect to a reference point.

Once the movable clamp assembly 120 has been moved to its desired position along the longitudinal axis 111 of the rail body housing 110, the lead bolt 112 can be secured against further rotation with the installation of an actuator screw cap, or other such mechanism, which locks the angular position of the lead bolt 112. For instance, a wave spring can be can be inserted into the actuator opening 217 (see FIG. 3) at the actuator end of the rail body 110. The wave spring may be followed by the actuator screw cap which is threaded into the actuator opening 217 until the wave spring is compressed between the head of the lead bolt 112 and the inside face of the actuator screw cap. This compression of the wave spring can create a self-locking friction fit which prevents rotation of the lead bolt 112. If desired, the actuator screw cap can also include depressions which allow for the deformation of the threads of the actuator screw cap into the threads formed into the actuator opening 217, further securing the actuator screw cap, wave spring and lead bolt 112 against inadvertent rotation.

Figure 2:
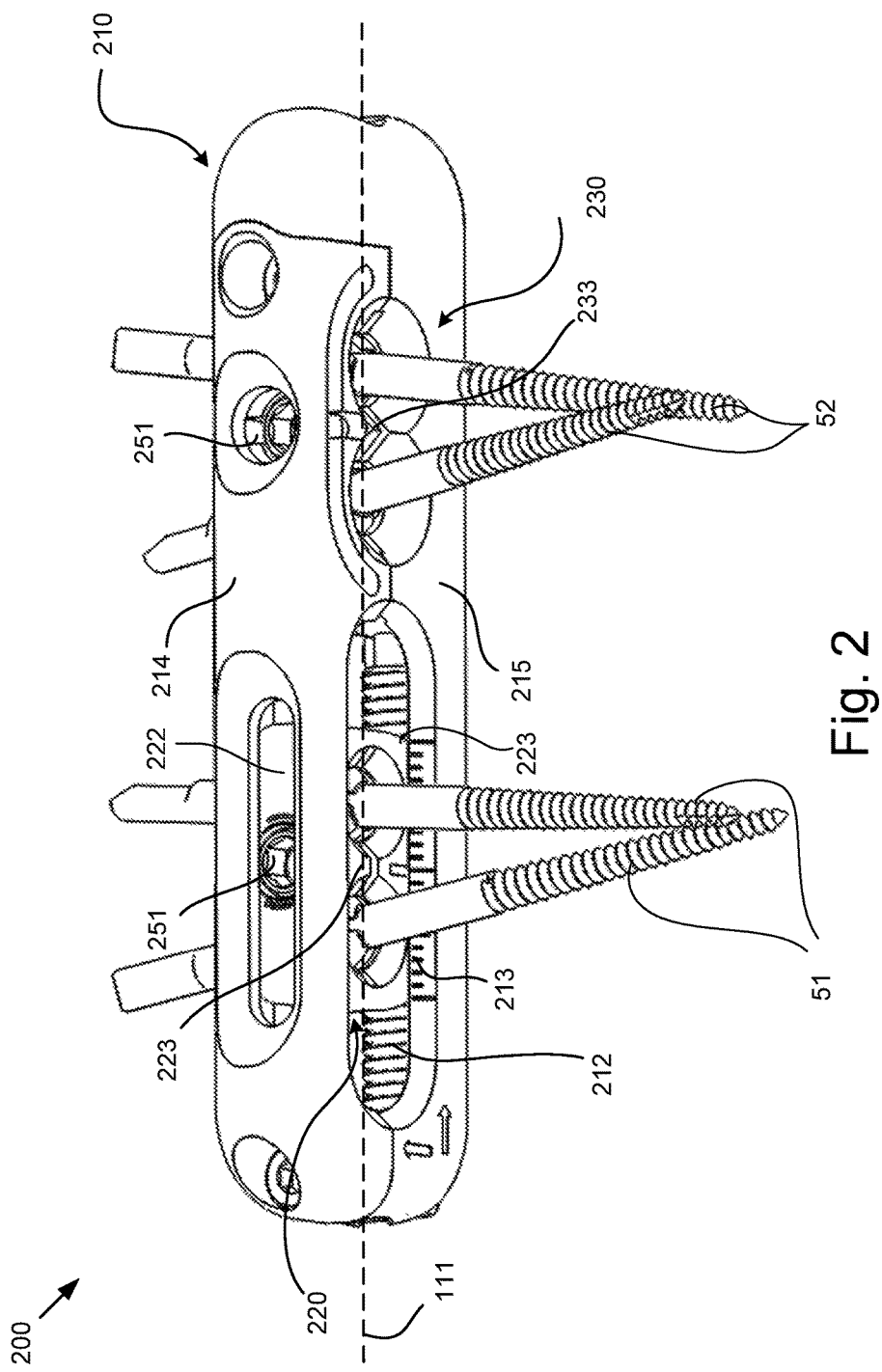
FIG. 2 is a perspective view of another embodiment of the bone fixation device that includes a movable clamp assembly and a fixed clamp assembly.

FIG. 2 is a perspective view of another embodiment of a bone fixation device 200 that includes a movable clamp assembly 220 and a fixed clamp assembly 230 within a rail body housing 210. As described above, bone fasteners 51, 52 may be inserted through and secured by the clamp assemblies 220, 230. Many if not most of the components of the fixed clamp assembly 230 can be similar to the components of the movable clamp assembly 220, with the differences being related to how the clamp assemblies 220, 230 are coupled to the rail body housing 210. The fixed clamp assembly 230 is translationally fixed within the rail body housing 220. For example, the top clamp member and bottom clamp member of the fixed clamp assembly 230 may be integrally formed with the top portion 214 and the bottom portion 215 of the housing 210, respectively. More specifically, the top clamp member of the fixed clamp assembly 230 may form a monolithic one-piece construction with the top portion 214 of the housing 210, and the bottom clamp member of the fixed clamp assembly 230 forms a monolithic one-piece construction with the bottom portion 214 of the housing 210. To facilitate tightening of the top clamp member of the fixed clamp assembly 230 against the bottom clamp member of the fixed clamp assembly (e.g. clamping down on a semi-spherical collet 241), a slot 290 is formed in the top portion 214 of the housing 210. The slot 290 allows the top clamp member of the fixed clamp assembly 230 to flex relative to the top portion 214 of the housing, thereby facilitating the clamping action of the fixed clamp assembly 230 relative to the housing 210. Although described in greater detail below, the term "semi-spherical collet" does not refer to a hemispherical (i.e., a half a sphere) object but instead refers generally to a spherical, ball-shaped structure.

The movable clamp assembly 220 and the fixed clamp assembly 230 secure at least one first bone fastener 51 and at least one second bone fastener 52. As depicted in the figures of the present disclosure and according to one embodiment, each clamp assembly 220, 230 may include a clamping mechanism 223, 233 that secures two bone fasteners 51, 52.

Each clamping mechanism 223, 233 of the clamp assemblies 220, 230 may include one or collar mechanisms for holding and securing bone fasteners, also known as a bone pin. The collar mechanisms 223, 233 have a hole to align the bone fastener with a target location on the patient's bone. In one aspect, the collar mechanism of the clamp assemblies can also function as a jig for aligning a drill bit to drill the bone at the target location. The bone fasteners can then be screwed into the bone of the patient. The bone fasteners can be rotated about their own longitudinal axis within the unclamped collar mechanism as it is screwed into the bone 2, prior to tightening the clamp assembly.

In one embodiment, each clamp assembly 220, 230 may include a clamp nut 251 or clamp fastener. With a single mechanical action, the turning of the clamp nut 251 can provide the clamping of the one or more collar mechanisms about the bone fasteners. This can provide a distinct advantage to a user or surgeon for positioning and holding a clamp assembly and/or bone fasteners in one hand while turning the clamp nut 251 with the other. However, it is considered that other devices and methods for activating the clamping function of clamping mechanisms 223, 233 about the bone fasteners are also possible and considered to fall within the scope of the present disclosure, including those in which each clamping function is activated separately via separate clamping components.

In the illustrated embodiment, each clamping mechanism 223, 233 may allow for the bone fasteners 51, 52 to be independently tilted up and down and side to side (e.g., joystick-like motion). In other words, the first bone fasteners 51 may be tilted and oriented independent of the second bone fasteners 52. In another embodiment, each bone fastener of the multiple (i.e., two) bone fasteners 51 in the movable clamp assembly 220 may be tilted and oriented independent of the other bone fasteners in the same clamp assembly 220. The same bone fastener orientation independence may be true for the fixed clamp assembly 230 and the second bone fasteners 52.

In one embodiment, the location of the clamp assemblies 220, 230 within the rail body housing 210 (as opposed to extending from or translationally coupled to a side of the rail body housing) improves the secure clamping of the bone fasteners and imparts comparatively improved balance to the bone fixation device. For example, if the clamp assemblies 220, 230 were not housed within the rail body housing 210 and were instead coupled or mounted to the side of the rail body housing, the offset forces along the bone fasteners may impart unequal and/or unbalanced torsional forces on the rail body housing. These unbalanced torsional forces may strain the integrity of the rail body housing and the clamp assemblies and/or the mechanical strain may be imparted to the bones of a patient via the bone fasteners, thus creating undesired torsional stress and strain on the healing bone.

Figure 3:
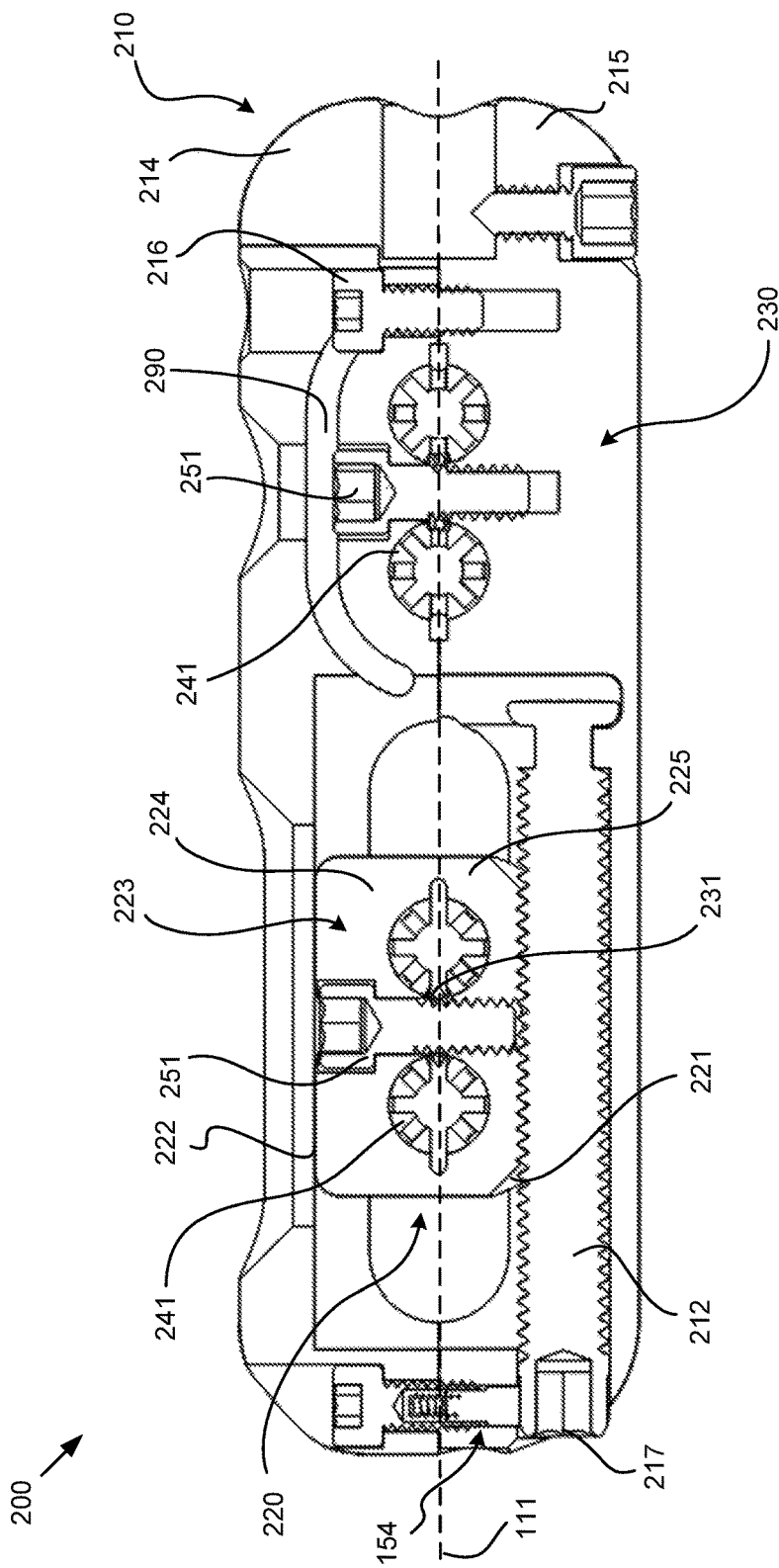
FIG. 3 is a cross-section view of the bone fixation device of FIG. 2, according to one embodiment.

FIG. 3 is a cross-section view of the bone fixation device 200 of FIG. 2, according to one embodiment. In one embodiment, the clamping mechanisms 223, 233 may each include a top clamp member 224 and a bottom clamp member 225 with a semi-spherical collet 241 disposed in between the top and bottom clamp members 224, 225 (see FIG. 3). The top and bottom clamp members 224, 225 may be separable structures or may be portions of an integrated structure that is clampable/compressible about the semi-spherical collets 241. To facilitate the compressible structure of the clamping mechanism 223. 233 of the clamp assemblies 220, 230, a notch or kerf wedge 231 (i.e., compression slot) may be formed between the top and bottom clamp members 224, 225. In one embodiment, a clamping fastener or clamping bolt 251 may be actuated to compress the clamping mechanisms. In one embodiment, the clamping bolt 251 does not directly engage the socket or the bone fastener, but instead engages the structure of the clamping assembly and cause the structure of the clamping assembly to partially compress/collapse to apply a clamping pressure on the bone fasteners.

The top and bottom clamp members 224, 225, which may be similar to the collar mechanisms described above, may each have curved clamping surfaces that cumulatively form a socket that houses the semi-spherical collet 241 (or multiple sockets and multiple semi-spherical collets). The curved clamping surfaces allow the semi-spherical collets 241 (and secured bone fasteners) to be tilted and oriented as desired. Additional details relating to the semi-spherical collets 241 are described below with reference to FIGS. 7A-8.

As briefly described above, the moving clamp assembly 220 has a carriage portion and a clamping mechanism 223 portion. Since the movable clamp assembly 220 is moveably coupled within the rail body housing 210, the movable clamp assembly 220 may have a threaded carriage portion 221 and a sliding carriage portion 222. The threaded carriage portion 221, according to one embodiment, is a threaded, concave bottom surface of the movable clamping assembly 220. The threaded, concave bottom surface may have thread dimensions and a curvature that correspond to the thread dimensions and curvature of the lead bolt 212, thereby allowing the threaded bottom surface of the movable clamp assembly 220 to rest upon the lead bolt 212. The sliding carriage portion 222 may be slidably received by a slot or a groove in the top portion 214 of the rail body housing 210.

In addition to the top surface of the sliding portion 222 being slidably engaged on the top portion 214 (e.g., within a groove/slot) of the rail body housing 210 and the concave bottom surface of the carriage portion 221 being engaged on the lead bolt 212, internal sidewalls of the rail body housing may also at least partially engage lateral external surfaces of the movable clamp assembly 220, thus preventing the movable clamp assembly 220 from slipping out of alignment with the longitudinal axis 111 of the rail body housing 210. In other words, as described above, securing the top portion 214 of the rail body housing 210 to the bottom portion 215 may not only include clamping down on the top sliding portion 222 and the bottom carriage portion 223 (via the lead bolt), but the top and bottom portions 214, 215 of the rail body housing may form a partial enclosure laterally around the lateral external surfaces of the movable clamp assembly 220, thereby preventing movement of movable clamp assembly 220 in a direction other than along the longitudinal axis 111 of the rail body housing.

As defined above, the longitudinal axis 111 is the axis that extends through a center of the rail body housing 210 and that is substantially parallel to the lead bolt 212. The center of the rail body housing 210 can be a center-of-gravity of the rail body housing, or a midpoint between a thickness of the housing and height of the housing, or a geometric center of the rail body housing. Further, in certain implementations, the clamp assemblies are positioned within the rail body housing 210 such that the longitudinal axis 111 extends through a center (e.g., geometric center, center of gravity) of each of the semi-spherical collets 241 of the clamp assemblies.

In one aspect of the bone fixation device 200, the rail body housing can include other types of translation mechanisms for precisely translating the movable clamp assembly 220 relative to the rail body housing 210. The rail body housing 210 may further include a rotational index indicator 154 that indicates, whether audibly, palpably, and/or visually, actuation of the lead bolt 212 and the corresponding translation of the movable clamp assembly 220. Details relating to the rotational index indicator 154 are included below with reference to FIGS. 6A-6B.

In some embodiment, the movable carriage portion 36 and lead bolt are similar to a previous design for a bone fixation device which was patented by the present inventor and disclosed in U.S. Pat. No. 7,507,250, which issued on Mar. 24, 2009, and which is incorporated herein by reference in its entirety.

Figure 4A:
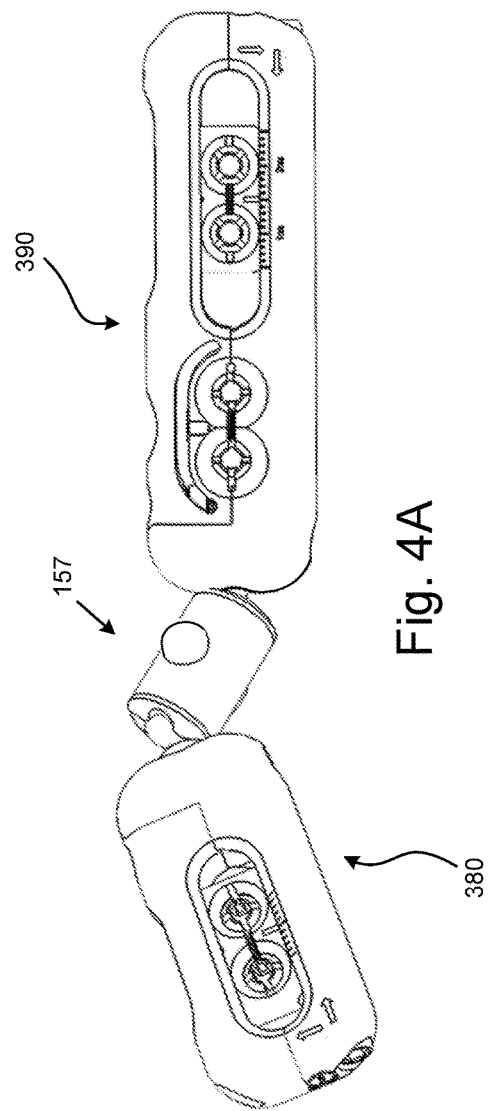
FIG. 4A is a perspective view of one embodiment of a bone fixation system.
Figure 4B:
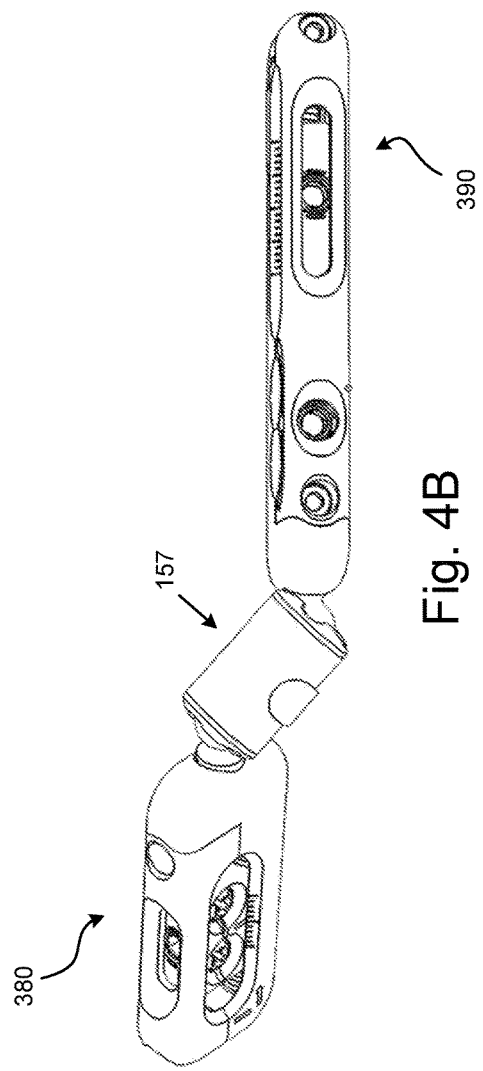
FIG. 4B is a side perspective view of one embodiment of the bone fixation system of FIG. 4A.

FIG. 4A is a perspective view of one embodiment of a bone fixation system. In one embodiment, multiple rail body housings 380, 390 may be coupled together to form a bone fixation system. In one embodiment, the rail body housings 380, 390 are coupled together via a ball joint or other similar mechanism that further allows a user to position the rail body housings 380, 390 in a desired orientation. For example, as shown in FIGS. 4A and 4B, the longitudinal axis of the rail body housings 380, 390, may be offset in a non co-linear fashion. In another embodiment, a coupler, such as a double ball joint 157 (described in greater detail below with reference to FIG. 4D), may be used to extend the rail body housings 380, 390 in parallel yet offset directions.

Figure 4C:
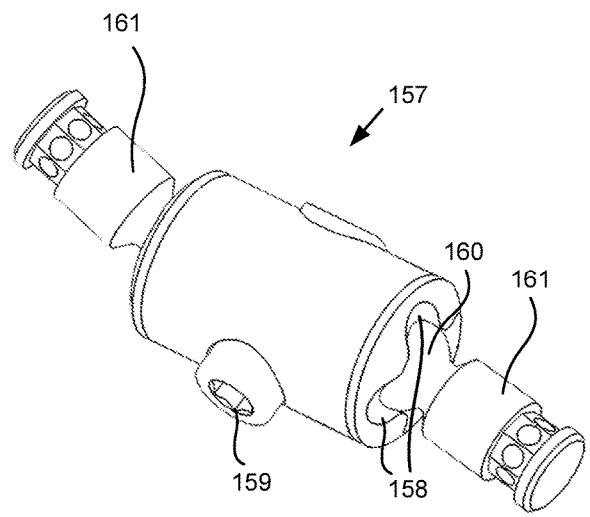
FIG. 4C is one embodiment of a double ball joint that can be used in the bone fixation system of FIG. 4A.

In one embodiment, the rail body housings 380, 390 may be coupled together via a double ball joint 157. FIG. 4C shows one embodiment of a double ball joint 157 that can be used in the bone fixation system of FIG. 4A. The double ball joint 157 may include one or more end caps 158 that may have a plurality of lobes on an exterior surface of each end cap that orient the inter-coupled rail body housings 380, 390 in predetermined angular configurations. For example, the double ball joint 157 may include four lobes circumferentially spaced around each side of the double ball joint housing, wherein the coupler shafts 161 extending from partially enclosed ball portions 160 may be oriented to rest within one of the four lobes. The double ball joint 157 may further include a set screw 159 or other securing mechanism whereby the position and orientation of the ball portions 160 and/or coupler shafts 161 are securely maintained.

Figure 4D:
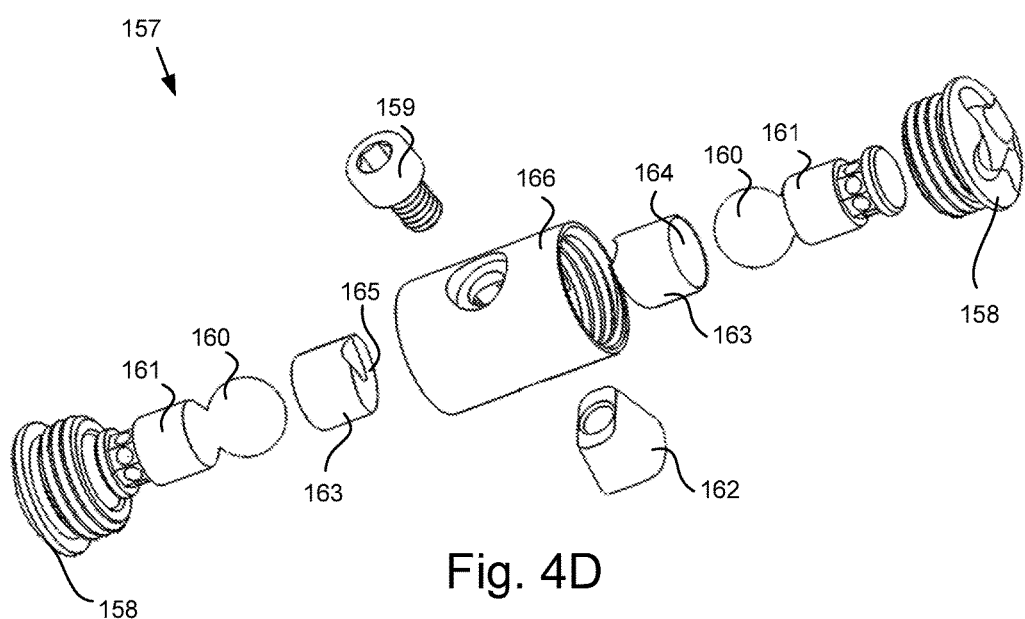
FIG. 4D is an exploded view of one embodiment of a double ball joint that can be used in the bone fixation system of FIG. 4A.

FIG. 4D is an exploded view of one embodiment of a coupler that is a double ball joint 157 that can be used in the bone fixation system of FIG. 4A and FIG. 4E is a perspective cross-sectional view of the double ball joint 157. With reference to FIGS. 4D and 4E, the double ball joint 157 may include a set screw 159 that is threadably coupled to a wedge component 162 within a housing 166. As the set screw 159 is tightened (e.g., rotated), the wedge component 162 is drawn further into the housing 166 in the direction 167, and an angled surface 169 of the wedge component 162 engages (i.e., presses against) a first surface 165 of a ball engagement element 163. The ball engagement element 163 also has a second surface 164, which may be an articular curved surface, opposite the first surface 165, that engages the spherical surface of the ball portion 160. As the wedge component 162 is drawn into the housing 166 in the direction 167, engagement between the first surface 165 of the ball engagement element 163 and the angled surface 169 of the wedge component 162 urges the ball engagement element 163 to move outwardly away from the set screw 159 in the direction 171.

The outward movement of the ball engagement element 163 in the direction 171 caused by the retraction of the wedge component 162 presses the ball portion 160 into contact with the lobed end cap 158 that is coupled to the housing 166. In one embodiment, the end cap 158 may have an inwardly slanted surface 168 that retains the ball portion 160 of the ball joint. In other words, the ball portion 160 is retained between the ball engagement feature 163 and the end cap 158, which may have various circumferentially spaced lobes, thus enabling a user to couple together various rail body housings in various predetermined configurations according to the needs of a specific application. As described further below, the details of this specific embodiment of the double ball joint 157 may be adapted and/or combined with other joint mechanisms for coupling rail body housings together. For example, a joint mechanism that includes a fixed coupler shaft on one end and a ball joint coupler shaft on the other end may be utilized in certain applications.

Figure 5:
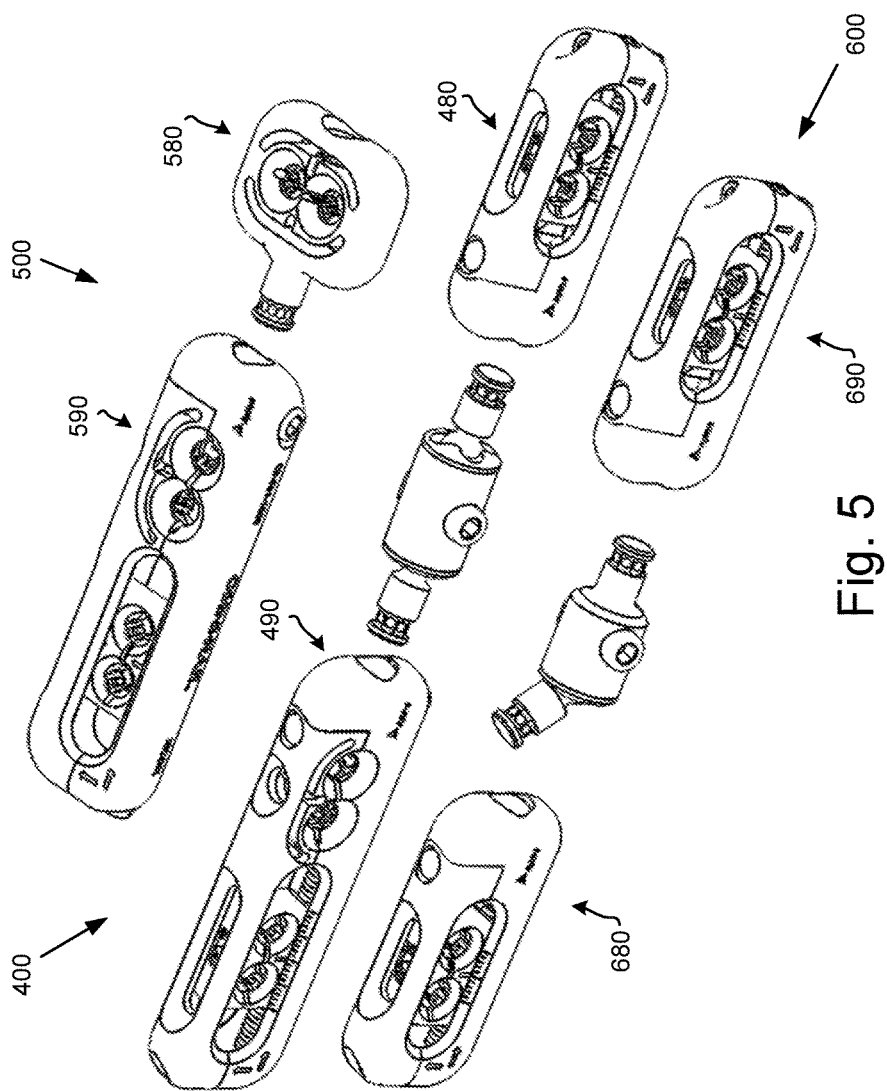
FIG. 5 depicts several embodiments of rail body housings configurations.

FIG. 5 depicts several embodiments of rail body housing configurations 400, 500, 600. The first exemplary configuration 400 shows two rail body housings 481, 490 coupled together at an angle. As described above, not only may two rail body housings 480, 490 be coupled together in a non co-linear orientation but the rail body housings 480, 490 may extend in non-parallel directions. The first configuration 400 includes a first rail body housing 480 that has a single, movable clamp assembly and a second rail body housing 490 that two clamp assemblies (one fixed and one movable). The second configuration 500 of FIG. 5 shows a rail body housing 580 that includes a single fixed clamp assembly coupled to a second rail body housing 590 that includes a fixed and movable clamp assembly. The third configuration 600 of FIG. 5 shows two rail bodies 680, 690 coupled together that each include a single, movable clamp assembly. It is expected that other configurations and other combinations of various rail body housings may be implemented, according to the specifics of a given application. Such other configurations and combinations fall within the scope of the present disclosure. For example, the rail body may be coupled to or implemented in conjunction with conventional splint devices.

FIG. 6 is a perspective view of one embodiment of the rotational index indicator 154. As described above, the movable clamp assembly 220 has a threaded carriage portion 221 that corresponds and engages the lead bolt 612. The actuation/rotation of the lead bolt 612 causes the movable clamp assembly 220 to translate along the lead bolt 612. The rotational index indicator 154 may be included to, for example, audibly indicate actuation of the lead bolt 612 and the corresponding translation of the movable clamp assembly 220. The rotational index indicator 154 may be coupled to the lead bolt 612 and/or may be partially integrated within a channel of the rail body housing. The rotational index indicator 154 may include a pin 156 and a biasing element. The pin 156, which may be a traditional pin or may be a tongue or blade-type structure, is disposed to be in contact with grooves 155A, 155B that are circumferentially spaced apart on the exterior surface of a portion of the lead bolt 612. For example, the lead bolt may have a first groove 155A and a second groove 155B that is circumferentially spaced-apart from the first groove 155A. With the pin engaged with the first groove 155A, rotation of the lead bolt overcomes a bias of the biasing element to disengage the pin from the first groove 155A and causes the pin to engage the second groove 155B.

The rotation of the lead bolt 612 and the resulting rise and fall of the spring loaded pin 156 as it engages the spaced apart grooves 155A, 155B produces a clicking sound that provides auditory feedback to the user. For example, the bone fixation device may be configured so that one full rotation (i.e., 360 degrees) of the lead bolt 612 results in a longitudinal translation of the movable clamp assembly 220 a certain distance (e.g., 1 millimeter). Accordingly, a practitioner may perform (or ask a patient to perform) periodic adjustment procedures to move the movable clamp 220 to a new position. The user may rotate the lead bolt 612 until he has heard a certain number of "clicks", thereby indicating a certain translational distance.

Figure 7A:
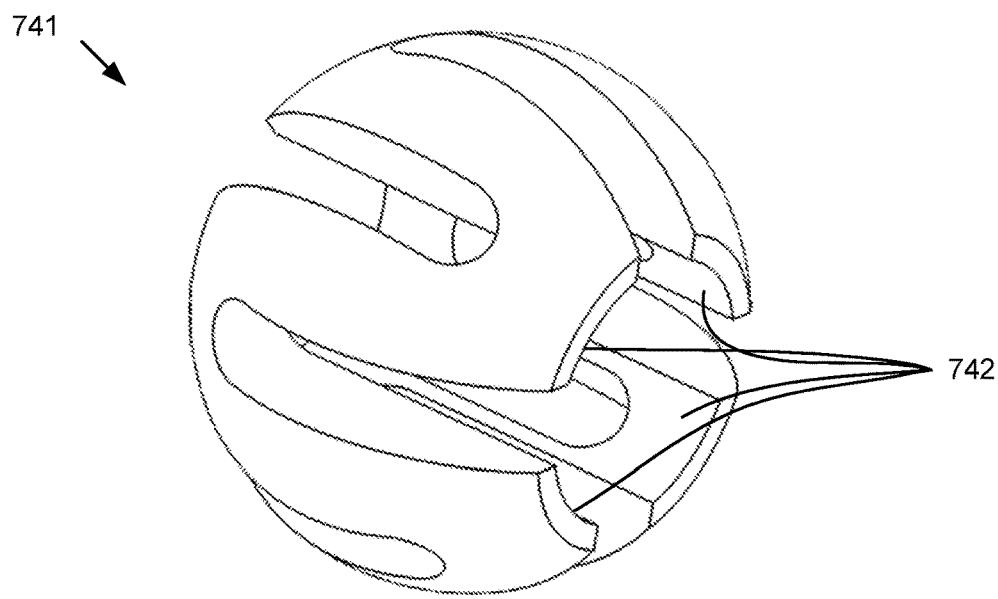
FIG. 7A is a perspective view of one embodiment of a semi-spherical collet.
Figure 7B:
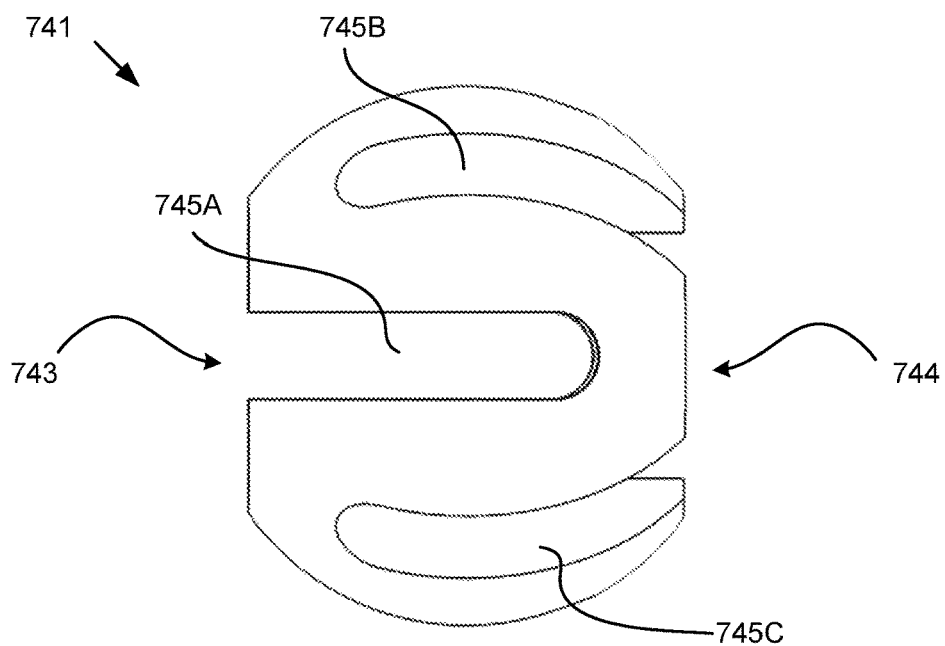
FIG. 7B is a side view of the semi-spherical collet of FIG. 7A, according to one embodiment.

FIG. 7A is a perspective view of one embodiment of a semi-spherical collet 741 that is disposed within a socket formed by the clamping mechanism of a clamp assembly. FIG. 7B is a side view of the semi-spherical collet 741 of FIG. 7A, according to one embodiment. The semi-spherical collet 741 is rotatably supported in the socket of a clamping mechanism. The semi-spherical collet 741, according to one embodiment, has a central channel 742 that extends through a diameter of the semi-spherical collet 741. The central channel 742 forms a borehole that has a first opening 743 and a second opening 744. The semi-spherical collet may also include a plurality of grooves 745A, 745B, 745C that extend from the first and second openings 743, 744. In one embodiment, the grooves 745A, 745B, 745C extend in a substantially radial direction from the exterior surface of the semi-spherical collet 741 to the central channel. Further, the grooves 745A, 745B, 745C may have an alternating configuration, with each of the grooves 745A, 745B, 745C extending in a circumferential direction from either the first or second opening across the surface of the semi-spherical collet 741 to a region circumferentially adjacent the other opening. The design of the depicted grooves facilitates even compression and locking about a bone fastener that is inserted through the central channel 742. It is expected that other groove designs and/or configurations may be implemented to achieve the compression of the ball sockets about the bone fasteners.

Figure 8:
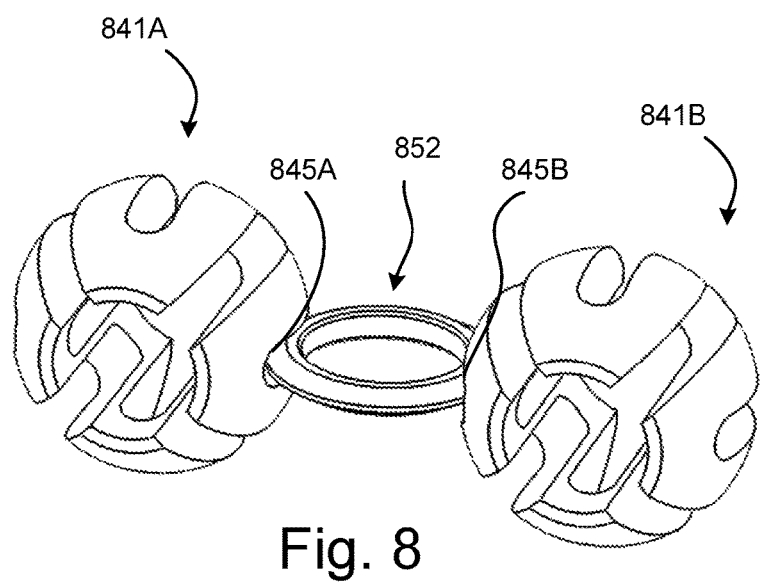
FIG. 8 is a perspective view of one embodiment of a rotational locking ring.

FIG. 8 is a perspective view of one embodiment of a rotational locking ring 852. In one embodiment, the clamping mechanisms may include a rotational locking ring 852 that prevents certain ranges of motion between two adjacent semi-spherical collets 841A, 841B. For example, the rotational locking ring 852 may be disposed between the adjacent semi-spherical collets 841A, 841B so that a portion of the locking ring 852 intersects or engages a notch 845A, 845B in the semi-spherical collets 841A, 841B. The notch 845A, 845B may be independent from the apertures described above or the notch 845A, 845b may refer to the apertures themselves. In one embodiment, the rotational locking ring 852 is configured to merely limit rotation of the semi-spherical collets 841A, 841B in certain directions but may substantially entirely prevent rotation in other directions. For example, in one embodiment the engagement between the rotational locking ring 852 and the notches 845A, 845B limits the rotation of the semi-spherical collets 841A, 841B so that the central channel remains accessible for insertion of bone fasteners while preventing rotation of the semi-spherical collets 841A, 841B about the central axis of the central channel. In one embodiment, the locking ring 852 may be chamfered or may have beveled opposing surfaces that facilitate engagement with the notch 845A, 845B.

In another embodiment, the engagement of the rotational locking ring 852 between the semi-spherical collets 841A, 841B may rotationally couple the two semi-spherical collets 841A, 841B together, thus ensuring that the semi-spherical collets 841A, 841B are uniformly oriented and/or tilted. The rotational locking ring 852 may be especially useful for drill jig applications to prevent rotation of the semi-spherical collets about the central channel and/or in applications when the central channels of the semi-spherical collets need be parallel to each other. It is expected that other mechanisms may be implemented to rotationally lock two or more adjacent semi-spherical collets together in order to ensure that the semi-spherical collets are all positioned, tilted, and oriented uniformly.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:
1. A bone fixation device, comprising:
   a rail body housing comprising a top portion, bottom portion, first end portion, second end portion, and a rail channel extending along a longitudinal axis of the rail body housing, wherein the rail channel is defined between the top portion, bottom portion, first end portion, and second end portion; and
   a movable clamp assembly movably coupled to the rail body housing within the rail channel, the position of the movable clamp assembly within the rail channel being adjustable, the movable clamp assembly comprising:
      at least two semi-spherical collets each defining a central channel configured to receive a bone fastener and orient the bone fastener in any of a plurality of orientations with respect to the rail body housing;
      a size of the central channel is adjustable to retain the bone fastener therein, and wherein a central axis of the central channel intersects the longitudinal axis of the rail body housing; and
      means for coupling the at least two semi-spherical collets together to prevent rotation of the at least two semi-spherical collets about respective central channels of the at least two semi-spherical collets.

2. The bone fixation device of claim 1, wherein the longitudinal axis passes through a geometric center of the rail body housing.

3. The bone fixation device of claim 1, further comprising a fixed clamp assembly longitudinally fixed relative to the rail body, the fixed clamp assembly comprising at least one semi-spherical collet defining a central channel configured to receive a bone fastener, wherein the size of the central channel is adjustable to retain the bone fastener therein, and wherein a portion of the rail body housing is flexible to adjust the size of the central channel.

4. The bone fixation device of claim 3, wherein a central axis of the central channel of the at least one semi-spherical collet of the fixed clamp assembly intersects the longitudinal axis of the rail body housing.

5. The bone fixation device of claim 1, further comprising a lead bolt extending parallel to the longitudinal axis within the rail body housing, and wherein:
the lead bolt is threadably engaged with the movable clamp assembly;
rotation of the lead bolt causes the movable clamp assembly to move along the longitudinal axis within the rail body housing;
the rail body housing comprises a top portion and a bottom portion detachably coupled together;
the bottom portion comprises a first groove and the top portion comprises a second groove;
the lead bolt is retained within the first groove; and
a bottom portion of the movable clamp assembly is threadably engaged and rests on the lead bolt and a top portion of the movable clamp assembly is slidably engaged in the second groove.

6. The bone fixation device of claim 1, further comprising a lead bolt extending parallel to the longitudinal axis within the rail body housing, and wherein:
the lead bolt is threadably engaged with the movable clamp assembly;
rotation of the lead bolt causes the movable clamp assembly to move along the longitudinal axis within the rail body housing;
the rail body housing comprises a first groove;
the lead bolt is retained within the first groove; and
the movable clamp assembly comprises a second groove that threadably engages and only partially encircles the lead bolt.

7. The bone fixation device of claim 1, wherein:
the rail body housing comprises a top portion and a bottom portion detachably coupled together; and
the longitudinal axis extends between the top portion and the bottom portion of the rail body housing.

8. The bone fixation device of claim 1, further comprising a lead bolt extending parallel to the longitudinal axis within the rail body housing, and wherein:
the lead bolt is threadably engaged with the movable clamp assembly; rotation of the lead bolt causes the movable clamp assembly to move along the longitudinal axis within the rail body housing; and
the lead bolt comprises an actuator screw cap actuatable to rotatably lock the rotational position of the lead bolt and the translational position of the movable clamp assembly.

9. A bone fixation device, comprising:
a rail body housing comprising a first end portion, a second end portion, and a rail channel extending along a longitudinal axis of the rail body housing, wherein the rail channel is defined between the first end portion and the second end portion;
a movable clamp assembly movably coupled to the rail body housing within the rail channel, the position of the movable clamp assembly within the rail channel being adjustable;
a lead bolt extending parallel to the longitudinal axis within the rail body housing, wherein the lead bolt is threadably engaged with the movable clamp assembly, and wherein rotation of the lead bolt causes the movable clamp assembly to move along the longitudinal axis within the rail body housing; and
a rotational index indicator coupled to the lead bolt, the rotational index indicator audibly and/or palpably indicating incremental rotation of the lead bolt and incremental translation of the movable clamp assembly;
wherein the lead bolt comprises at least one groove formed in an exterior surface of the lead bolt, and the rotational index indicator comprises:
a pin; and
a biasing element coupled to the pin, the biasing element biasing the pin into engagement with the at least one groove, wherein rotation of the lead bolt causes the pin to engage and disengage from the at least one groove, engagement between the pin and the at least one groove generating an audible and/or a palpable response.

10. The bone fixation device of claim 9, wherein:
the at least one groove comprises a first groove and a second groove circumferentially spaced-apart from the first groove;
with the pin engaged with the first groove, rotation of the lead bolt overcomes a bias of the biasing element to disengage the pin from the first groove and causes the pin to engage the second groove.

11. The bone fixation device of claim 9, wherein:
the at least one groove comprises at least four grooves equally and circumferentially spaced apart from each other; and
a circumferential distance between each of the four grooves corresponds with a predetermined translational displacement of the movable clamp assembly.

12. A bone fixation device for treating deformation of bones, comprising:
a rail body housing comprising a top portion, bottom portion, first end portion, second end portion, and a rail channel extending along a longitudinal axis of the rail body housing, wherein the rail channel is defined between the top portion, bottom portion, first end portion, and second end portion, the bottom portion of the rail body housing comprising a lead bolt;
a movable clamp assembly movably coupled within the rail body housing for securing two first bone fasteners in a first desired orientation, the movable clamp assembly being translatable along the lead bolt within the rail body housing, the movable clamp assembly comprising a carriage portion that is threadably engaged on the lead bolt and a clamping mechanism that is adapted to secure the first bone fasteners, wherein the clamping mechanism comprises two semi-spherical collets supported within two sockets, wherein the semi-spherical collets are independently adjustable relative to each other, wherein the first bone fasteners extend through a central channel in each of the semi-spherical collets, and wherein a central axis of the central channel intersects the longitudinal axis of the rail body housing;
a fixed clamp assembly coupled within the rail body housing for securing two second bone fasteners in a second desired orientation, the fixed clamp assembly being translationally fixed within the rail body housing, the fixed clamp assembly comprising a clamping mechanism that is adapted to secure the second bone fasteners, wherein the clamping mechanism comprises two semi-spherical collets supported within two sockets, wherein the semi-spherical collets are independently adjustable relative to each other, wherein the second bone fasteners extend through a central channel in each of the semi-spherical collets; and a rotational index indicator that audibly and/or palpably indicates rotation of the lead bolt, wherein the rotational index indicator is integrated with the rail body housing and coupled to the lead bolt.

13. The bone fixation device of claim 1, further comprising:

at least two semi-spherical sockets, wherein each of the at least two semi-spherical collets is retained by a corresponding one of the at least two sockets, wherein a size of the central channel is adjustable to retain the bone fastener therein, wherein each of the at least two semi-spherical collets comprises at least one groove; and a ring fixed relative to the at least two semi-spherical sockets, the ring configured to engage the at least one groove of each of the at least two semi-spherical collets to restrict rotation of the semi-spherical collets about the corresponding central channel of the semi-spherical collets.

14. The bone fixation device of claim 13, wherein the central channel of each of the at least two semi-spherical collets extends through a diameter of the semi-spherical collet, the central channel comprising a first opening and a second opening, wherein the at least one groove of each of the at least two semi-spherical collets comprises a plurality of apertures that extend between the first and second openings, wherein each of the apertures extends in a radial direction from an exterior surface to the central channel and in a circumferential direction from one of the first opening and the second opening to a region circumferentially adjacent the other of the first opening and the second opening.

15. The bone fixation device of claim 13, wherein each of the at least two semi-spherical collets is configured to apply a substantially uniform clamping pressure around an exterior surface portion of the corresponding bone fastener.

16. The bone fixation device of claim 13, wherein the at least two semi-spherical collets orient the bone fasteners in any of a plurality of orientations with respect to the at least two semi-spherical sockets.

17. The bone fixation device of claim 1, further comprising a double ball joint coupleable to the rail body housing, the double ball joint comprising:

a double ball joint housing;

a first end cap coupled to a first end of the double ball joint housing;

a set screw at least partially within the double ball joint housing;

a wedge component at least partially within the double ball joint housing, the wedge component threadably receiving the set screw, wherein as the set screw is tightened, the wedge component moves in a first direction relative to the double ball joint housing;

a first ball engagement element at least partially within the double ball joint housing, the first ball engagement element comprising a first surface and a second surface, wherein the first surface is engaged with the wedge component; and a first ball joint comprising a ball portion and a shaft portion, the ball portion being at least partially disposed within the double ball joint housing between the second surface of the first ball engagement element and the first end cap, the first end cap being between the shaft portion and the first ball engagement element, wherein as the wedge component moves into engagement with the first ball engagement element, the first ball engagement element moves the ball portion of the first ball joint towards the first end cap to retain the ball portion of the first ball joint between the second surface of the first ball engagement element and the first end cap.

18. The bone fixation device of claim 17, wherein the rail body housing is coupleable to the shaft portion of the first ball joint, wherein when coupled to the double ball joint the rail body housing is positionable in any of a plurality of predetermined orientations relative to the double ball joint housing.

19. The bone fixation device of claim 18, wherein:

the first end cap comprises a plurality of lobes defining a plurality of receptacles circumferentially spaced apart; and the shaft portion of the ball joint is receivable within any of the plurality of receptacles to securely position the shaft portion of the ball joint in any of a plurality of predetermined orientations.

20. The bone fixation device of claim 18, wherein:

the double ball joint housing defines a longitudinal axis; and each of the plurality of predetermined orientations forms a 45-degree angle with the longitudinal axis of the housing.

21. The bone fixation device of claim 17, further comprising:

a second end cap coupled to a second end of the double ball joint housing;

a second ball engagement element at least partially within the double ball joint housing, the second ball engagement element comprising a first surface and a second surface, wherein the first surface is engaged with the wedge component; and a second ball joint comprising a ball portion and a shaft portion, the ball portion being at least partially disposed within the double ball joint housing between the second surface of the second ball engagement element and the second end cap, the second end cap being between the shaft portion and the second ball engagement element, wherein as the wedge component moves into engagement with the second ball engagement element, the second ball engagement element moves the ball portion of the second ball joint towards the second end cap to retain the ball portion of the second ball joint between the second surface of the second ball engagement element and the second end cap.

* * * * *